(12) United States Patent
Zhu et al.

(10) Patent No.: US 7,709,649 B2
(45) Date of Patent: *May 4, 2010

(54) MULTI-SUBSTITUTED PYRIDYL SULFOXIMINES AND THEIR USE AS INSECTICIDES

(75) Inventors: Yuanming Zhu, Carmel, IN (US); Michael R. Loso, Carmel, IN (US); Benjamin M. Nugent, Brownsburg, IN (US); Jim X. Huang, Carmel, IN (US); Richard B. Rogers, Mobile, AL (US)

(73) Assignee: Dow AgroSciences LLC, Indianapolis, IN (US)

( * ) Notice: Subject to any disclaimer, the term of this patent is extended or adjusted under 35 U.S.C. 154(b) by 93 days.

This patent is subject to a terminal disclaimer.

(21) Appl. No.: 11/704,820

(22) Filed: Feb. 9, 2007

(65) Prior Publication Data
US 2008/0108667 A1    May 8, 2008

Related U.S. Application Data

(60) Provisional application No. 60/857,611, filed on Nov. 8, 2006.

(51) Int. Cl.
*C07D 213/56* (2006.01)
*A61K 31/44* (2006.01)

(52) U.S. Cl. .................................. 546/338; 514/357
(58) Field of Classification Search ................ 546/338; 514/357
See application file for complete search history.

(56) References Cited

U.S. PATENT DOCUMENTS

| | | | | |
|---|---|---|---|---|
| 4,053,622 | A * | 10/1977 | Kollmeyer | 514/385 |
| 4,833,158 | A | 5/1989 | Twydell et al. | |
| 6,060,502 | A * | 5/2000 | Lowder et al. | 514/424 |
| 2005/0228027 | A1 | 10/2005 | Zhu et al. | |
| 2009/0023782 | A1* | 1/2009 | Babcock | 514/336 |

OTHER PUBLICATIONS

Reinhard et al Molecules 2005, 101369-1376.*
U.S. Appl. No. 11/704,397, filed Feb. 9, 2007, Jim X. Huang, et al.
U.S. Appl. No. 11/704,756, filed Feb. 9, 2007, Kim E. Arndt, et al.
U.S. Appl. No. 11/704,759, filed Feb. 9, 2007, Stephen T. Heller, et al.
U.S. Appl. No. 11/704,796, filed Feb. 9, 2007, Kevin G. Meyer, et al.
U.S. Appl. No. 11/704,797, filed Feb. 9, 2007, Michael R. Loso, et al.
U.S. Appl. No. 11/704,824, filed Feb. 9, 2007, Jim X. Huang, et al.
U.S. Appl. No. 11/704,825, filed Feb. 9, 2007, James M. Renga, et al.
U.S. Appl. No. 11/704,842, filed Feb. 9, 2007, Michael R. Loso, et al.
U.S. Appl. No. 11/704,853, filed Feb. 9, 2007, Michael R. Loso, et al.
U.S. Appl. No. 11/705,185, filed Feb. 9, 2007, Michael R. Loso, et al.
International Search Report for PCT/US2007/003780, Sep. 17, 2007, Dow AgroSciences LLC [Yuanming Zhu et al.].
Written Opinion of the International Searching Authority for PCT/US2007/003780, Sep. 17, 2007, Dow AgroSciences LLC [Yuanming Zhu et al.].
Kagabu, Shinzo and Medej, Somporn; "Stability Comparison of Imidacloprid and Related Compounds under Simulated Sunlight, Hydrolysis Conditions, and to Oxygen;" Biosci. Biotech. Biochem., 59 (6), 980-985, (1995).
Kollmeyer, Willy D.; Flattum, Roger F.; Foster, James P.; Powell, James E.; Schroeder, Mark E. and Soloway, S. Barney; "Discovery of the Nitromethylene Heterocycle Insecticides;" Nicotinoid Insecticides and the Nicotinic Acetylcholine Receptor [Eds.: Yamamoto, I. and Casida, J.E.]; 1999, pp. 71-89, Springer-Verlag, Tokyo.
Sparks, Thomas C.; Crouse, Gary D. and Durst, Gregory; "Natural products as insecticides: the biology, biochemistry and quantitative structure-activity relationships of spinosyns and spinosoids;" Pest Management Science, 57:896-905 (2001).
Shiga, Yasushi; Okada, Itaru and Fukuchi, Toshiki; "Synthesis and Acaricidal Activity of N-(1,3,4-Thiadiazol-2-yl)cyclopropanecarboxamides;" J. Pesticide Sci. 28, 61-63 (2003).
Wakita, Takeo; Kinoshita, Katsutoshi; Kodaka, Kenji; Yasui, Naoko; Naoi, Atsuko and Banba, Sinichi; "Synthesis and Structure-Activity Relationships of Dinotefuran Derivatives: Modification in the Tetrahydro-3-furylmethyl Part;" J. Pesticide Sci. 29 (4), 356-363 (2004).
Kagabu, Shinzo; Murata, Natsue; Hibino, Rika; Hanzawa, Madoka and Nishimura, Keiichiro; "Insecticidal and Neuroblocking Activities of Thiamethoxam-Type Compounds in the American Cockroach (*Periplaneta americana* L.);" J. Pesticide Sci. 30(2), 111-115 (2005).

* cited by examiner

*Primary Examiner*—Janet L. Andres
*Assistant Examiner*—John Mabry
(74) *Attorney, Agent, or Firm*—Carl D. Corvin; Craig E. Mixan

(57) ABSTRACT

Multi-substituted pyridyl sulfoximines are useful as insecticides.

7 Claims, No Drawings

MULTI-SUBSTITUTED PYRIDYL SULFOXIMINES AND THEIR USE AS INSECTICIDES

This application claims the benefit of U.S. Provisional Application Ser. No. 60/857,611 filed on Nov. 8, 2006.

BACKGROUND OF THE INVENTION

The present invention concerns novel multi-substituted pyridyl sulfoximines and their use in controlling insects, particularly aphids and other sucking insects, as well as certain other invertebrates. This invention also includes new synthetic procedures for preparing the compounds, pesticide compositions containing the compounds, and methods of controlling insects using the compounds.

There is an acute need for new insecticides. Insects are developing resistance to the insecticides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides. Therefore a need exists for new insecticides, and particularly for compounds that have new or atypical modes of action.

U.S. Patent Application Publication 2005/0228027 A1 describes certain sulfoximine compounds including some containing mono-substituted pyridine groups and their use in controlling insects. It has now been discovered that sulfoximines bearing multi-substituted pyridines have comparable or improved insecticidal activity.

SUMMARY OF THE INVENTION

This invention concerns compounds useful for the control of insects, especially useful for the control of aphids and other sucking insects. More specifically, the invention concerns compounds of the formula (I)

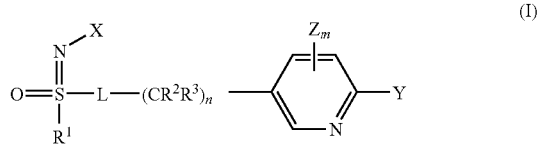

(I)

wherein
X represents CN, $NO_2$, or $COOR^4$, $CONR^5R^6$ or $COR^5$;
Y represents halogen, $C_1$-$C_4$ alkyl, $C_1$-$C_4$ haloalkyl, $C_1$-$C_4$ alkoxy, $C_1$-$C_4$ haloalkoxy, CN, $NO_2$, $R^1S$, $R^1SO$—, $R^1SO_2$—, $COOR^4$ or $CONR^5R^6$;
Z represents halogen, azido, $C_1$-$C_4$ alkyl, $C_1$-$C_4$ alkoxy, $C_1$-$C_4$ haloalkyl, $C_1$-$C_4$ haloalkoxy, aryl or heteroaryl;
m represents an integer from 1-3;
L represents either a single bond or $R^1$, S and L taken together represents a 4-, 5- or 6-membered ring;
$R^1$ represents $C_1$-$C_4$ alkyl, $C_1$-$C_4$ haloalkyl, arylalkyl, heteroarylalkyl, $C_3$-$C_6$ alkenyl, $C_3$-$C_6$ haloalkenyl, or $C_3$-$C_6$ alkynyl, or —$CH_2$— in cases where $R^1$, S and L taken together represent a 4-, 5-, or 6-membered ring;
$R^2$ and $R^3$ independently represent hydrogen, halogen, $C_1$-$C_4$ alkyl, $C_1$-$C_4$ haloalkyl, $C_1$-$C_4$ alkoxy, ($C_1$-$C_4$ alkoxy) $C_1$-$C_4$ alkyl, arylalkyl, or heteroarylalkyl, or $R^2$, C and $R^3$ taken together form a 3-, 4-, 5- or 6-membered ring optionally containing an O or N atom;
n represents an integer from 0-3; and $R^4$, $R^5$ and $R^6$ each independently represent hydrogen, $C_1$-$C_4$ alkyl, $C_1$-$C_4$ haloalkyl, aryl, or heteroaryl.

Preferred compounds of formula (I) include the following classes:

(1) Compounds of formula (I) wherein Z is halogen, most preferably monohalo (m=1).

(2) Compounds of formula (I) wherein X is $NO_2$ or CN, most preferably CN.

(3) Compounds of formula (I) wherein $R^2$ and $R^3$ independently represent hydrogen or $C_1$-$C_4$ alkyl, most preferably hydrogen, methyl or ethyl.

(4) Compounds of formula (I) wherein $R^1$, S and L taken together form a saturated 5-membered ring, and n is 0, i.e., having the structure

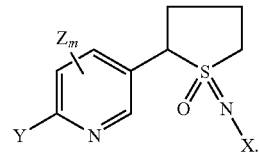

(5) Compounds of formula (I) wherein $R^1$ represents $CH_3$ and L represents a single bond, i.e., having the structure

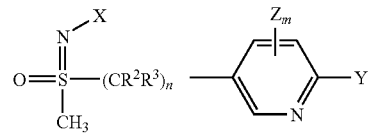

wherein n is an integer from 1-3, most preferably n=1.

(6) Compounds of formula (I) wherein Y represents halogen or $C_1$-$C_2$ haloalkyl, most preferably $C_1$ or $CF_3$.

It will be appreciated by those skilled in the art that the most preferred compounds are generally those which are comprised of combinations of the above preferred classes.

The invention also provides new processes for preparing compounds of formula (I) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated or volume percentages being used when the percentages are used for eluting mixed solvents in column chromatography.

The terms "alkyl", "alkenyl" and "alkynyl", as well as derivative terms such as "alkoxy", "acyl", "alkylthio", "arylalkyl", "heteroarylalkyl" and "alkylsulfonyl", as used herein, include within their scope straight chain, branched chain and cyclic moieties. Thus, typical alkyl groups are methyl, ethyl, 1-methyl-ethyl, n- or i-propyl, 1,1-dimethyl-ethyl, and cyclopropyl. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The term "haloalkyl" and "haloalkenyl" includes alkyl and alkenyl groups substituted with from one to the maximum possible number of halogen atoms, all combinations of halogens included. The term "halogen" or "halo"

includes fluorine, chlorine, bromine, and iodine, with fluorine and chlorine being preferred. The terms "alkenyl" and "alkynyl" are intended to include one or more unsaturated bonds.

The term "aryl" refers to a phenyl, indanyl or naphthyl group. The term "heteroaryl" refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more substituents selected from halogen, hydroxy, nitro, cyano, aryloxy, formyl, $C_1$-$C_6$ alkyl, $C_2$-$C_6$ alkenyl, $C_2$-$C_6$ alkynyl, $C_1$-$C_6$ alkoxy, halogenated $C_1$-$C_6$ alkyl, halogenated $C_1$-$C_6$ alkoxy, $C_1$-$C_6$ acyl, $C_1$-$C_6$ alkylthio, $C_1$-$C_6$ alkylsulfinyl, $C_1$-$C_6$ alkylsulfonyl, aryl, $C_1$-$C_6$OC(O)alkyl, $C_1$-$C_6$NHC(O)alkyl, C(O)OH, $C_1$-$C_6$C(O)Oalkyl, C(O)NH$_2$, $C_1$-$C_6$C(O)NHalkyl, or $C_1$-$C_6$C(O)N(alkyl)$_2$, provided that the substituents are sterically compatible and the rules of chemical bonding and strain energy are satisfied.

The compounds of this invention can exist as one or more stereoisomers. The various stereoisomers include geometric isomers, diastereomers and enantiomers. Thus the compounds of the present invention include racemic mixtures, individual stereoisomers and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

The compounds of formula (I), wherein $R^1$, $R^2$, $R^3$, $R^4$, $R^5$, $R^6$, X, Y and Z are as previously defined and L is a single bond, can be prepared by the methods illustrated in Scheme A:

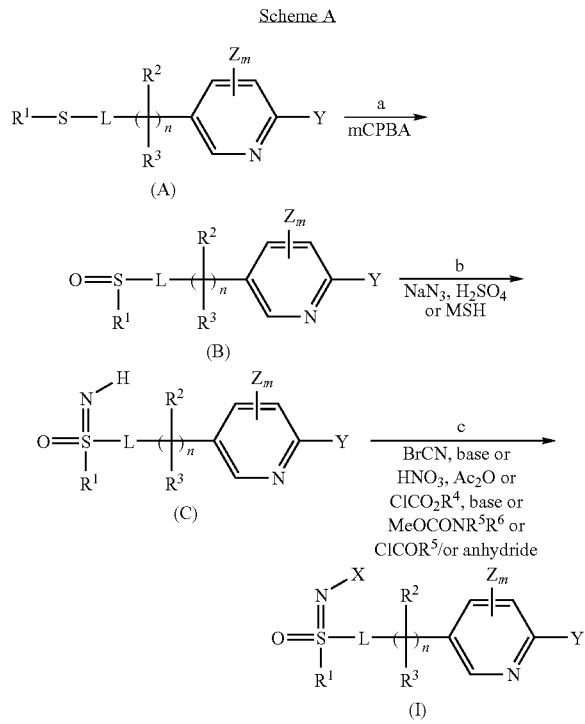

In step a of Scheme A, sulfide of formula (A) is oxidized with meta-chloroperoxybenzoic acid (mCPBA) in a polar solvent below 0° C. to provide sulfoxide of formula (B). In most cases, dichloromethane is the preferred solvent for oxidation.

In step b of Scheme A, sulfoxide (B) is iminated with sodium azide in the presence of concentrated sulfuric acid in an aprotic solvent under heating to provide sulfoximine of formula (C). In most cases, chloroform is the preferred solvent for this reaction. Sulfoximine of formula (C) can also be prepared from sulfoxide (B) using O-mesitylsulfonylhydroxylamine (MSH) in a polar aprotic solvent such as dichloromethane.

In step c of Scheme A, the nitrogen of sulfoximine (C) can be either cyanated with cyanogen bromide in the presence of a base, or nitrated with nitric acid in the presence of acetic anhydride under mildly elevated temperature, or carboxylated with alkyl ($R^4$) chloroformate in the presence of base such as 4-dimethylaminopyridine (DMAP) to provide N-substituted sulfoximine (I). Base is required for efficient cyanation and carboxylation and the preferred base for them is DMAP, or triethylamine, or pyridine, whereas sulfuric acid is used as catalyst for efficient nitration reaction. Sulfoximine (C) can also be acylated with an acyl chloride or (mixed) anhydride in the present of a base or without a base, or it can form a urea-like structure by reacting with methyl or ethyl carbamate.

The compounds of formula (Ia), wherein X represents CN and m, Y, $R^1$, $R^2$, $R^3$, L, Z are as previously defined, can be prepared by the mild and efficient method illustrated in Scheme B.

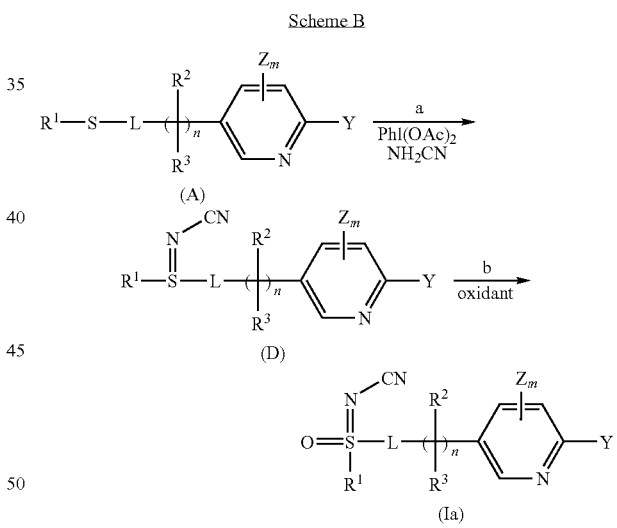

In step a of Scheme B, sulfide is oxidized with iodobenzene diacetate in the presence of cyanamide at 0° C. to give sulfilimine (D). The reaction can be carried out in a polar aprotic solvent such as tetrahydrofuran (THF) or dichloromethane.

In step b of Scheme B, the sulfilimine (D) is oxidized with mCPBA in a solvent such as a mixture of ethanol or acetonitrile and water to increase the solubility of the sulfilimine starting material and the base employed. The sulfilimine (D) can also be oxidized with aqueous sodium or potassium periodinate solution in the presence of catalyst ruthenium trichloride hydrate or similar catalyst. The organic solvent for this catalysis can be polar aprotic solvent such as dichloromethane, chloroform, or acetonitrile.

The α-carbon of the N-substituted sulfoximine of formula (Ib), wherein n=1, L is a single bond, and the carbon adjacent to the N-substituted sulfoximine function is either mono- ($R^2 \neq H$) or non-substituted (when $R^2 = H$) can be further alkylated or halogenated ($R^3$) in the presence of a base such as potassium hexamethyldisilamide (KHMDS) or butyl lithium (BuLi) to give N-substituted sulfoximines of formula (Ic) wherein n=1, L is a single bond, and $R^1$, $R^2$, X, Y, Z and integer "m" are as previously defined, illustrated in Scheme C. In this scheme, G is an appropriate leaving group. The preferred leaving groups are iodide ($R^3$=alkyl), benzenesulfonimidyl ($R^3$=F), pentachloroethyl ($R^3$=Cl), and bromotetrachloroethyl ($R^3$=Br).

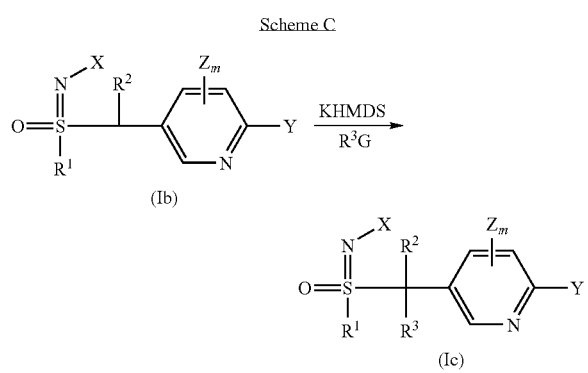

Sulfoximine compounds of formula (Id) wherein $R^1$, S and L taken together form a saturated 4-, 5- or 6-membered ring and n=1 can be prepared by the methods illustrated in Scheme D, wherein m, X, Y and Z are as previously defined and q is 0, 1, or 2.

In step b of Scheme D, similar to step c of Scheme A, the nitrogen of sulfoximine can be either cyanated with cyanogen bromide, or nitrated with nitric acid followed by treatment with acetic anhydride under refluxing conditions, or carboxylated with methyl chloroformate to provide N-substituted cyclic sulfoximine. Base is required for efficient cyanation and carboxylation and the preferred base is DMAP, whereas sulfuric acid is used as catalyst for efficient nitration reaction. The cyclic sulfoximine can also be acylated with an acyl chloride or (mixed) anhydride in the present of a base or without a base, or it can form a urea-like structure by reacting with methyl or ethyl carbamate under acidic conditions.

In step c of Scheme D, the α-carbon of N-substituted sulfoximine can be alkylated with a heteroaromatic methyl halide in the presence of a base such as KHMDS or BuLi to give the desired N-substituted sulfoximines. The preferred halide can be bromide, chloride or iodide.

Alternatively, the compounds of formula (Id) can be prepared by a first α-alkylation of sulfoxides to give α-substituted sulfoxides and then an imination of the sulfoxide followed by N-substitution of the resulting sulfoximine by using the steps c, a and b respectively as indicated above in Scheme D.

In certain cases it is advantageous to prepare sulfoximines of formula (I) from other sulfoximines. For example, the compounds of formula (If, Ig and Ih), wherein Y represents alkylthio, alkylsulfoxide and alkylsulfone respectively (alkyl exemplified by methyl) and m, n, $R^1$, $R^2$, $R^3$, L, X and Z are as previously defined, can be prepared from sulfoximine (Ie) where Y=halogen or any other appropriate leaving group (exemplified by Cl) as illustrated in Scheme E.

In step a of Scheme E, the α-leaving group (Cl) to the pyridine is substituted with sodium salt of an alkylthiol in polar solvent such as ethanol at room or elevated temperature

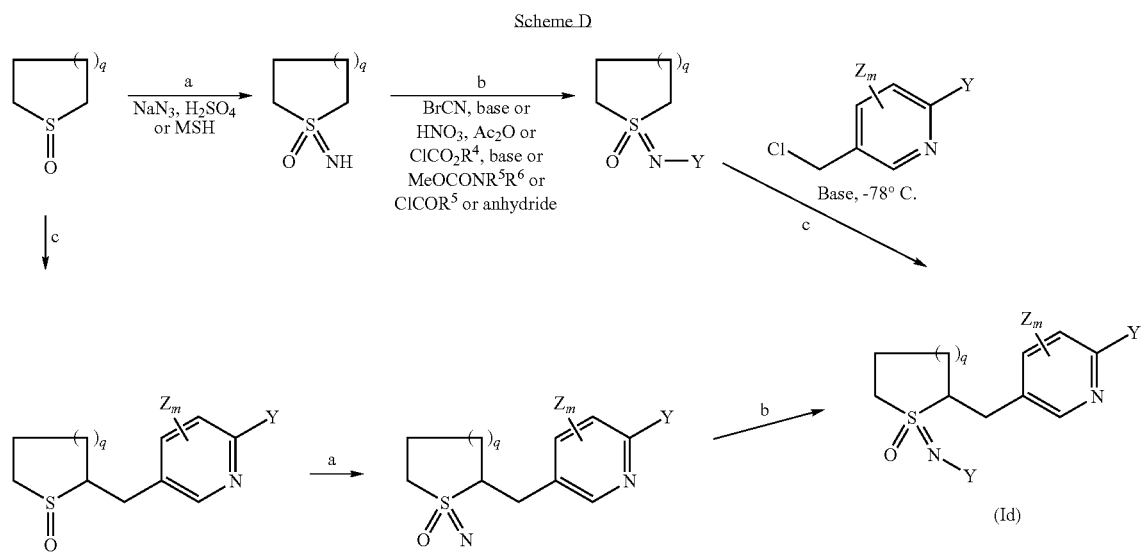

In step a of Scheme D, which is similar to step b of Scheme A, sulfoxide is iminated with sodium azide in the presence of concentrated sulfuric acid or with O-mesitylsulfonylhydroxylamine in a polar aprotic solvent to provide sulfoximine. Chloroform or dichloromethane are the preferred solvents.

to give alkylthio sulfoximine (If), which can be converted into the corresponding sulfoxide (Ig) and sulfone sulfoximine (Ih) respectively by mCPBA in polar solvent depending on the reaction temperature and the amount of the oxidant mCPBA used. The preferred solvent for the solvent is chloroform or dichloromethane.

Scheme E

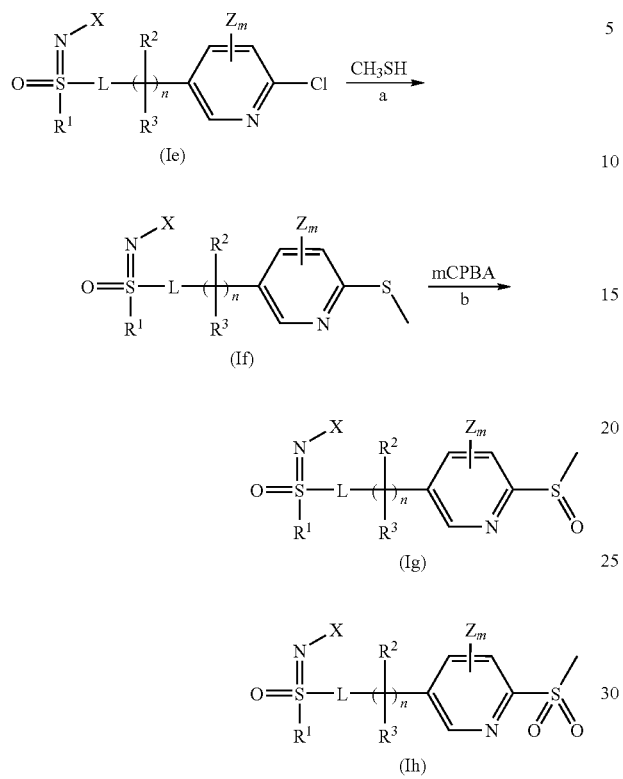

The starting sulfides (A) in Scheme A can be prepared in different ways as illustrated in Schemes F G, H, I, J, K and L.

In Scheme F, the sulfide of formula ($A_1$), wherein m, Z, $R^1$, $R^2$ and Y are as previously defined; L is a single bond; n=1; and $R^3$=H, can be prepared from the chloride of formula (E) by nucleophilic substitution with the sodium salt of an alkyl thiol. The reaction condition is similar to step a of Scheme E.

Scheme F

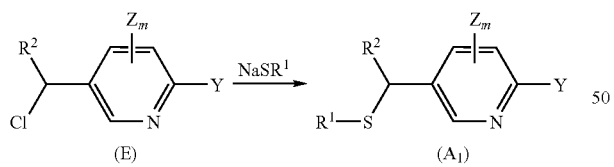

In Scheme G, the sulfide of formula ($A_2$), wherein m, Z, $R^1$, $R^2$ and Y are as previously defined, n=3, and $R^3$=H, can be prepared from the chloride of formula (F) by reacting with a 2-mono substituted methyl malonate in the presence of base such as potassium tert-butoxide to provide 2,2-disubstituted malonate, hydrolysis under basic conditions to form a diacid, decarboxylation of the diacid under heating to give a monoacid, reduction of the monoacid with borane-tetrahyrofuran complex to provide an alcohol, tosylation of the alcohol with toluenesulfonyl chloride (tosyl chloride or TsCl) in the presence of a base like pyridine to give a tosylate and replacement of the tosylate with the sodium salt of the desired thiol.

Scheme G

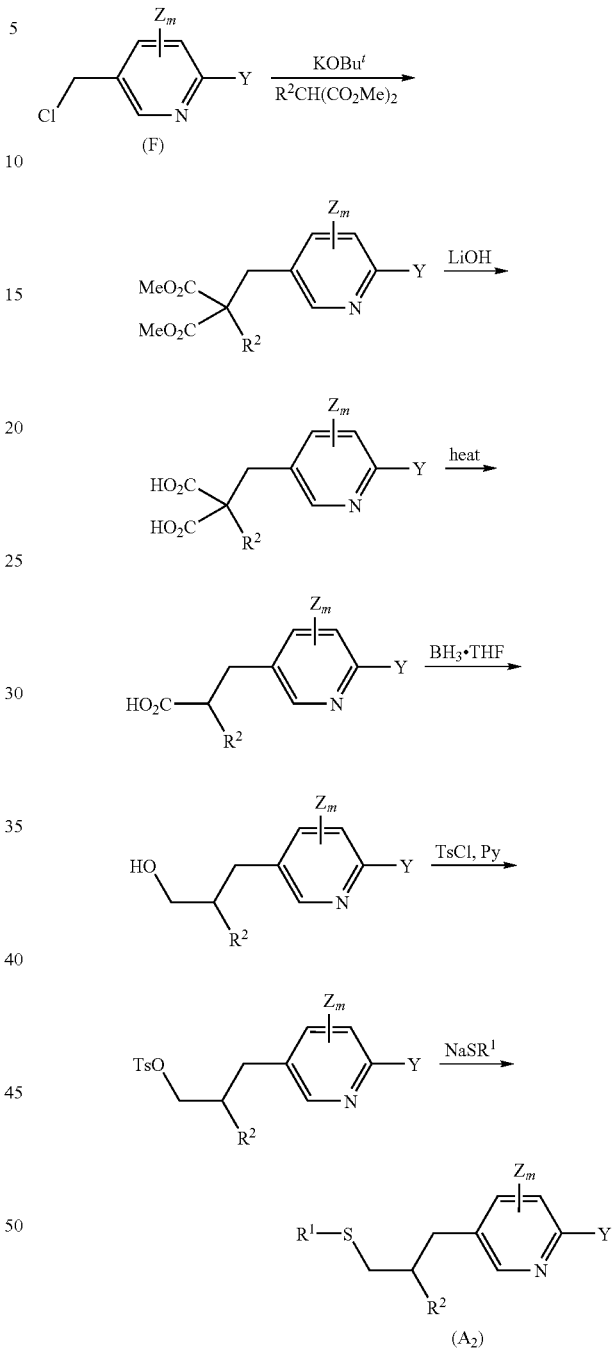

In Scheme H, the sulfide of formula ($A_3$), wherein m, Z, $R^1$, $R^2$ and Y are as previously defined, n=2, and $R^3$=H, can be prepared from the nitrile of formula (G) by deprotonation with a strong base and alkylation with an alkyl iodide to give α-alkylated nitrile, hydrolysis of the α-alkylated nitrile in the presence of a strong acid like HCl to give an acid, reduction of the acid with borane-tetrahyrofuran complex to provide an alcohol, tosylation of the alcohol with tosyl chloride in the presence of a base like pyridine to give a tosylate and replacement of the tosylate with the sodium salt of the desired thiol.

Scheme H

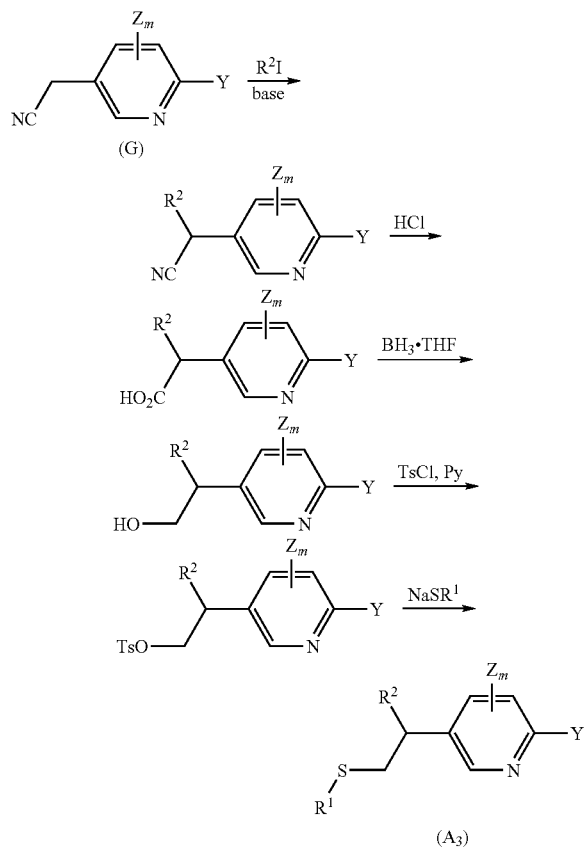

In Scheme I, the sulfide of formula ($A_4$), wherein m, Z and Y are as previously defined, $R^1$, S and L taken together represents a 4-, 5- or 6-membered ring (q=0, 1, or 2) and n is 0 can be prepared from the corresponding substituted halomethylpyridine exemplified by chloromethylpyridine by treatment with thiourea, hydrolysis and subsequent alkylation with the appropriate bromo chloroalkane (q=0, 1, or 2) under aqueous base conditions, and cyclization in the presence of a base like potassium-t-butoxide in a polar aprotic solvent such as THF.

Scheme I

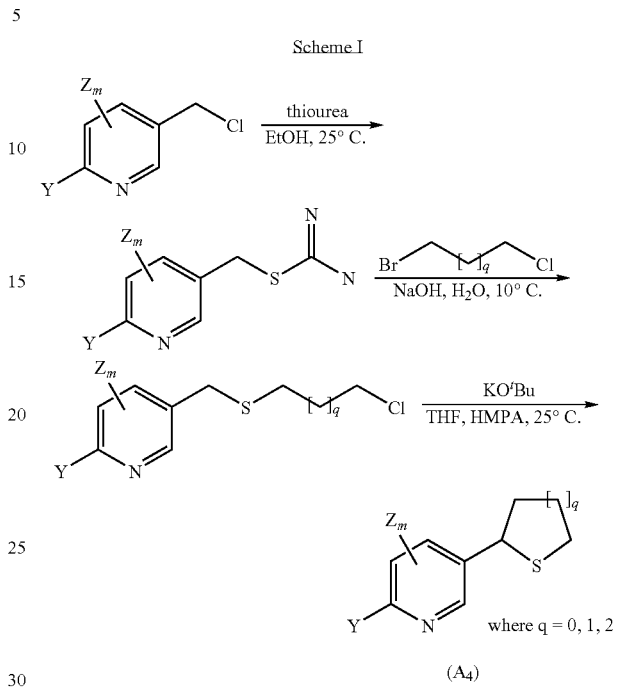

Sulfides of formula ($A_5$), wherein Z, $R^1$, $R^2$ and Y are as previously defined, and $Z^1$, $Z^2$ and $Z^3$ are the same as Z, can be prepared alternatively via methods illustrated in Scheme J. Accordingly, the appropriate enone ether is coupled with dimethylaminoacrylonitrile and cyclized with ammonium acetate in DMF to yield the corresponding 6-substituted (Y) nicotinonitrile. Treatment with alkylmagnesium bromide ($R^2$MgBr), reduction with sodium borohydride, chlorination with thionyl chloride, and nucleophilic substitution with the sodium salt of an alkyl thiol ($R^1$SH) provide desired sulfides ($A_5$).

Scheme J

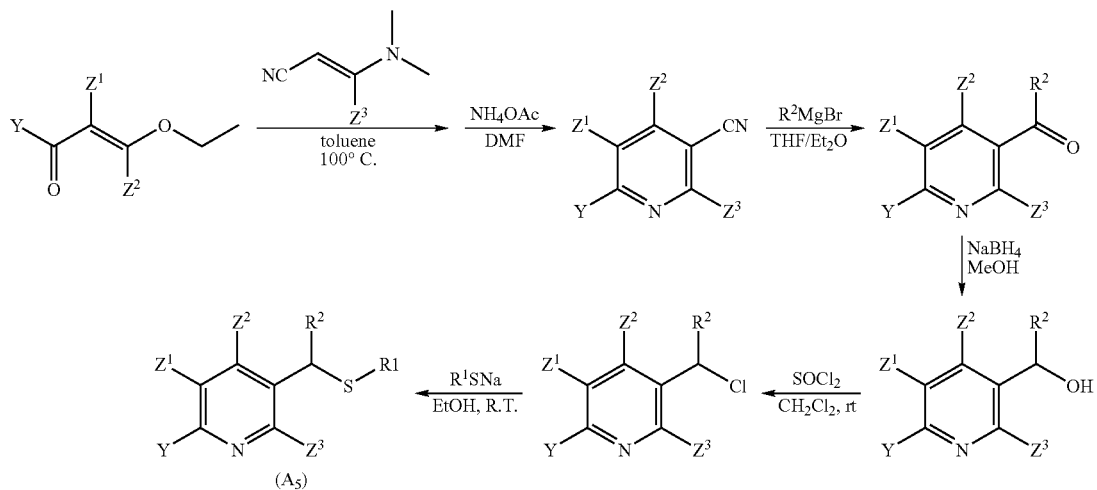

Sulfides of formula ($A_6$), wherein $R^1$, $R^2$, $R^3$, Y, $Z^1$, $Z^2$, and $Z^3$ are as previously described can also be prepared via a variation of Scheme J, depicted in Scheme K, wherein enamines, formed from the addition of an amine, e.g., pyrrolidine, with the Michael adduct of certain sulfides with appropriately substituted α,β-unsaturated aldehydes or ketones, are coupled with substituted enone ethers and cyclized with ammonium acetate in acetonitrile to yield the desired sulfides ($A_6$).

Scheme K

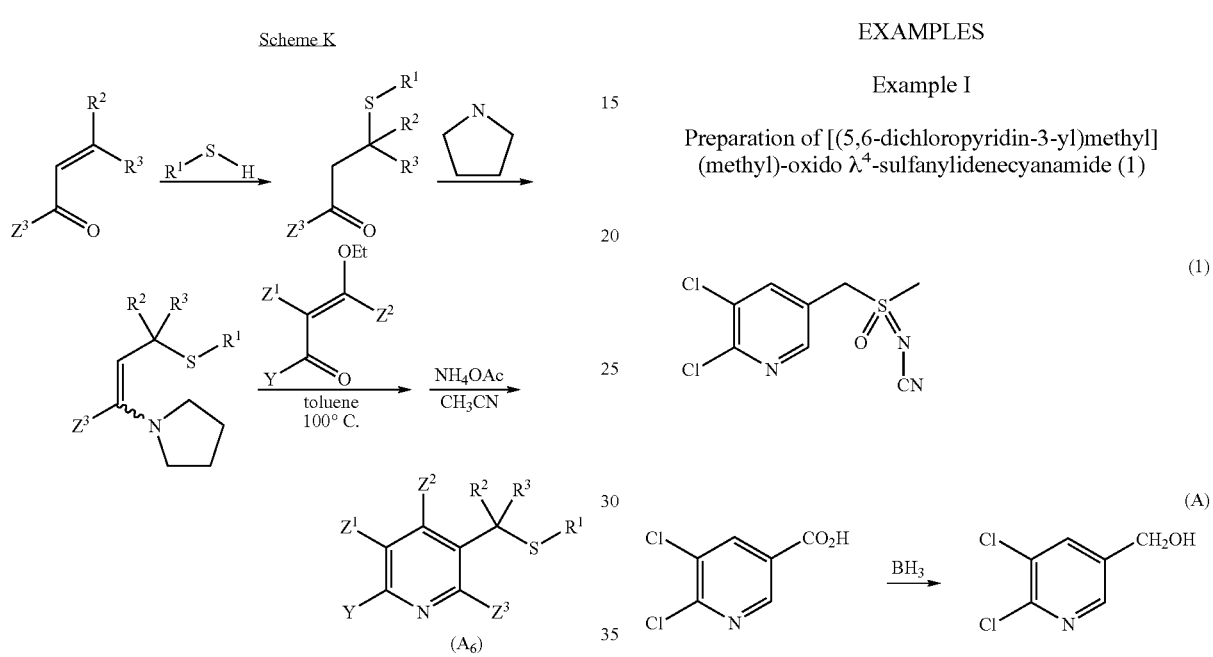

In Scheme L sulfides of formula ($A_7$) wherein $R^1$ and Y are as previously defined, n=1, and $R^2$, C and L taken together form a 4-, 5-, or 6-membered ring can be prepared from various substituted 5-bromo-pyridines via a halogen metal exchange with isopropyl Grignard reagent followed by addition to cyclic epoxides such as cyclopentene oxide (p=1). Subsequent conversion of the alcohol to sulfide ($A_7$) can be accomplished either by conversion to the chloride with phosphorous oxychloride and subsequent nucleophilic substitution with the sodium salt of an alkyl thiol, or by the reaction of the alcohol with a disulfide in the presence of triphenyl phosphine.

Scheme L

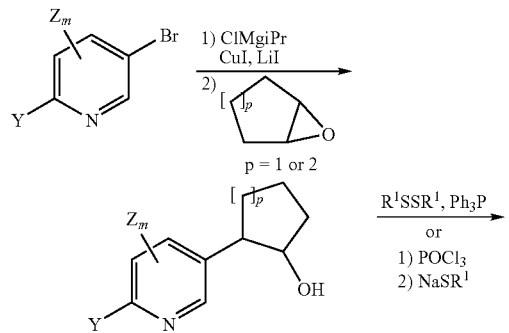

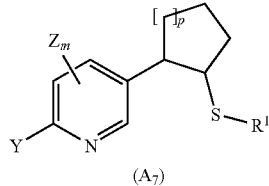

(A7)

EXAMPLES

Example I

Preparation of [(5,6-dichloropyridin-3-yl)methyl](methyl)-oxido $\lambda^4$-sulfanylidenecyanamide (1)

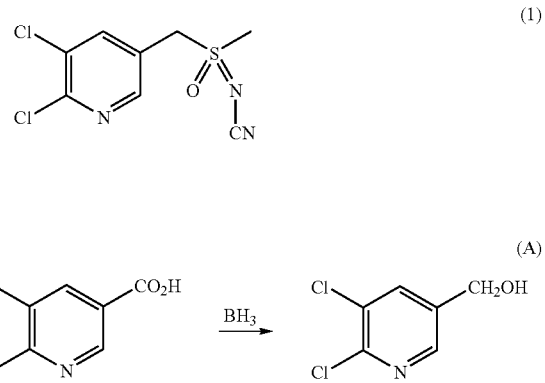

To a stirred solution of 5,6-dichloronicotinic acid (9.6 g, 50 mmol) in anhydrous tetrahydrofuran (THF; 50 mL) cooled in an ice-water bath was rapidly added 1 M $BH_3$ solution in THF (60 mL, 60 mmol) via a syringe. The mixture was stirred at 0° C. for 30 min while the mixture became orange in color and then at room temperature for 2 h. An additional portion of 1 M $BH_3$ solution in THF (50 mL, 50 mmol) was added and the mixture stirred at room temperature overnight. The mixture was then carefully poured into cold aqueous 1 N HCl solution (100 mL). The organic layer was separated and the aqueous layer extracted with dichloromethane. The combined organic layer was washed with water, dried over anhydrous $MgSO_4$, filtered, concentrated, and dried to give the desired 2,3-dichloro-5-hydroxymethylpyridine as a yellow oil. GC-MS: mass calcd for $C_6H_5Cl_2N$ [M]$^+$ 162. Found 162.

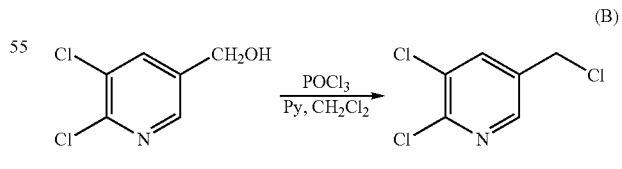

To a stirred solution of 2,3-dichloro-5-hydroxymethylpyridine (4.4 g, 25 mmol) and pyridine (2.61 g, 33 mmol) in dichloromethane (75 mL) was added rapidly phosphorous oxychloride (4.91 g, 32 mmol). An exothermic reaction sufficient to boil the reaction mixture ensued. After stirring at room temperature for 2 h, 1 N HCl aqueous solution (50 mL) was carefully added to the reaction mixture and the stirring continued for 10 min. The organic phase was separated and the aqueous phase extracted with dichloromethane (50 mL). The combined organic phase was washed successively with water (25 mL), 1 N aqueous NaOH solution (25 mL) and saturated aqueous NaCl solution (25 mL), dried over anhydrous $MgSO_4$, filtered, and concentrated to give 3.80 g of the desired 2,3-dichloro-5-chloromethylpyridine as yellow oil (77.4% yield) which solidified upon standing at room temperature. GC-MS: mass calcd for $C_6H_5Cl_2NO$ $[M]^+$ 178. Found 178

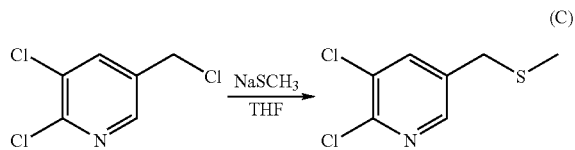
(C)

To a stirred solution of 2,3-dichloro-5-chloromethylpyridine (3.75 g, 19.1 mmol) in THF (30 mL) was added solid sodium thiomethoxide (2.01 g, 29 mmol) in one portion and the resulting mixture was stirred at room temperature for 3 h. The reaction mixture was diluted with ether (100 mL), washed with 0.1 N aqueous HCl (50 mL) solution and brine (50 mL), dried over anhydrous $MgSO_4$, filtered, concentrated, and dried to give 3.55 g of 2,3-dichloro-5-methylthiomethylpyridine as a dark yellow liquid in 89% crude yield. The crude product was analytically pure without further purification. GC-MS: calcd for $C_7H_7Cl_2NS$ $[M]^+$ 208. Found 208.

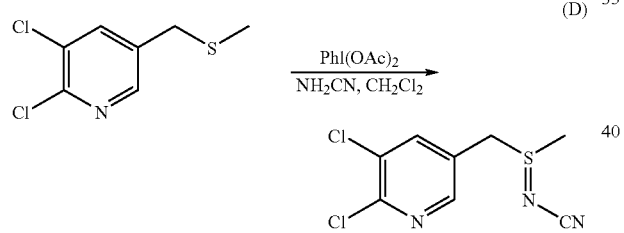
(D)

To a stirred solution of 2,3-dichloro-5-methylthiomethylpyridine (3.5 g, 16.8 mmol) and cyanamide (1.43 g, 34 mmol) cooled in an ice-water bath was added iodobenzenediacetate (6.76 g, 21 mmol) in one portion. The resulting mixture was stirred at 0° C. for 30 min and then continued at room temperature for 1 h. A solution of sodium bisulfite (2 g) in water (50 mL) was added and the organic phase separated. The aqueous phase was extracted with dichloromethane (2×50 mL). The combined organic phase was dried over $MgSO_4$ and the solvent evaporated to give a dark red oily residue which was triturated with boiling ether (2×40 mL) with the ether being discarded each time. After standing at room temperature overnight, the residue solidified, which was triturated with hot ethyl acetate (25 mL). Upon cooling down, the off-white solid product was collected by filtration and dried. Concentration of the filtrate and repeating the trituration process gave additional product. The total yield for the product [1-(5,6-dichloropyridin-3-yl)methyl](methyl)-$\lambda^4$-sulfanylidenecyanamide was 2.45 g (58.8%). LC-MS: calcd for $C_8H_7Cl_2N_3S$ $[M]^+$ 247. Found 247.

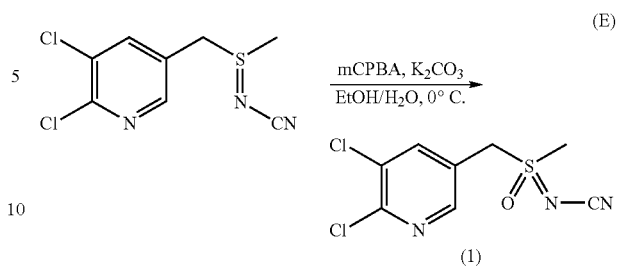
(E)

To a stirred solution of m-chloroperbenzoic acid (mCPBA; 80%, 3.48 g, 16.1 mmol) in EtOH (30 mL) at 0° C. was added a solution of $K_2CO_3$ (4.45 g, 32.2 mmol) in $H_2O$ (20 mL). The solution was stirred for 20 min and then a solution of [1-(5,6-dichloropyridin-3-yl)methyl](methyl)-$\lambda^4$-sulfanylidenecyanamide (2.0 g, 8.1 mmol) in EtOH (40 mL) was added all at once. The reaction was stirred at 0° C. for 30 minute and quenched with sodium bisulfite (1.5 g) in water (5 mL). The mixture was concentrated to remove ethanol. Water (50 mL) and additional $K_2CO_3$ (2 g) were added and the resulting mixture was extracted with EtOAc (3×75 mL). The combined organic layers was washed with brine (50 mL), dried over $MgSO_4$, filtered, and concentrated to give a crude white solid product (1.95 g, 91% yield). The crude product was recrystallized from ~1:1 methanol-water (v/v) (dissolved in 20-25 mL boiling methanol, then 15-20 mL water was added, followed by cooling in the freezer for 3 h) to give 1.55 g of the desired [(5,6-dichloropyridin-3-yl)methyl](methyl)-oxido-$\lambda^4$-sulfanylidenecyanamide (1) as a white solid in 72% yield. $^1$H NMR (300 MHz, $d_6$-DMSO) δ 8.47 (d, 1H), 8.22 (d, 1H), 5.16 (s, 2H), 3.48 (s, 3H). LC/MS calcd. for $C_8H_7Cl_2N_3OS$: 263. Found: 263.

Example II

Preparation of [(5-fluoro-6-chloropyridin-3-yl)methyl](methyl)-oxido-$\lambda^4$-sulfanylidenecyanamide (2)

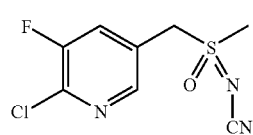
(2)

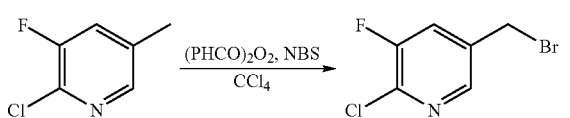
(A)

A suspension of 2-chloro-3-fluoro-5-methylpyridine (5.1 g, 35 mmol), N-bromosuccinimide (6.1 g, 35 mmol) and benzoylperoxide (0.16 g, 0.66 mmol) in carbon tetrachloride (100 mL) was refluxed overnight. Upon cooling down, the solid was filtered off and the filtrate was concentrated and loaded onto a silica gel column eluted with 5% EtOAc in hexane to give 3.77 g of the desired 2-chloro-3-fluoro-5- bromomethylpyridine as colorless oil in 48% yield. GC-MS calcd. for $C_6H_4BrClFN$: 224.46. Found: 224.

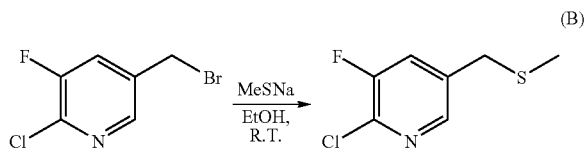

(B)

A solution of 2-chloro-3-fluoro-5-bromomethylpyridine (3.7 g, 16.5 mmol) in ethanol (40 mL) was treated with sodium thiomethoxide solid (2.31 g, 33 mmol) portionwise at 0° C. After the addition was over, the mixture was stirred at room temperature overnight. Most of the solvent ethanol was removed under reduced pressure and the residue was re-taken into dichloromethane. Brine solution was added and two phases mixed and separated. The organic layer was dried over anhydrous $Na_2SO_4$, filtered and concentrated. The resulting residue was purified on silica gel using 8% EtOAc in hexane as eluent to give 2.04 g of the desired 2-chloro-3-fluoro-5-methylthiomethylpyridine in 65% yield. GC-MS calcd. for $C_7H_7ClFNS$: 191.66. Found: 191.

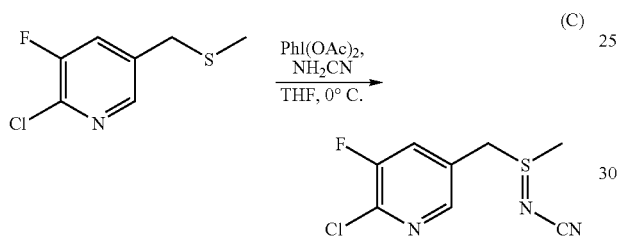

(C)

To a stirred solution of 2-chloro-3-fluoro-5-methylthiomethylpyridine (1.7 g, 8.9 mmol) and cyanamide (3.7 g, 8.9 mmol) in THF (15 mL) cooled to 0° C. was added iodobenzene diacetate (2.86 g, 8.9 mmol) in one portion and the resulting mixture was stirred at 0° C. for 1 h and then at room temperature for 2 h. The solvent was removed in vacuo and the resulting mixture was purified on silica gel using 60% acetone in hexane to give 1.828 g of [1-(5-fluoro-6-chloropyridin-3-yl)methyl](methyl)-λ$^4$-sulfanylidenecyanamide as an off-white solid in 89% yield. LC-MS calcd. for $C_8H_7ClFN_3S$ [M+1]$^+$: 232.69. Found: 232.04.

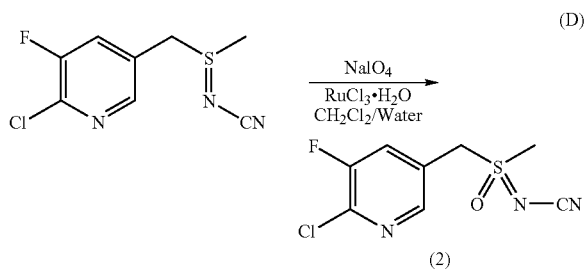

(D)

To a stirred solution of sodium periodate (1.44 g, 1.5 mmol) in water (20 mL) was added $CH_2Cl_2$ (20 mL) and ruthenium trichloride hydrate (0.049 g, 0.22 mmol). A solution of the [1-(5-fluoro-6-chloropyridin-3-yl)methyl](methyl)-λ$^4$-sulfanylidenecyanamide (1.04 g, 4.5 mmol) in dichloromethane (10 mL) was added through an addition funnel over a period of 30 min. The mixture was stirred rapidly at room temperature for 2 h and the starting material was consumed based on GC-MS. More dichloromethane was added and the mixture was filtered through a fritted glass filter with a pad of celite to remove some of the insolubles. The organic layer was collected and the aqueous layer was extracted with dichloromethane two times and ethyl acetate once. The combined organic layer was washed with brine, dried over anhydrous $Na_2SO_4$, filtered, and concentrated. The residue was purified on silica gel eluted with 35% acetone in hexane to give 0.645 g of [(5-fluoro-6-chloropyridin-3-yl)methyl](methyl)-oxido-λ$^4$-sulfanylidenecyanamide (2) as a white solid in 58% yield. $^1$H NMR (300 MHz, CDCl$_3$) δ 8.47 (m, 1H), 8.01-8.07 (m, 1H), 5.16 (m, 1H), 2.83-2.88 (m, 3H), 2.04-2.07 (m, 3H). LC-MS calcd. for $C_8H_7ClFN_3OS$ [M−1]$^+$: 246.67. Found: 245.95.

Example III

Preparation of [1-(5-fluoro-6-chloropyridin-3-yl)ethyl](methyl)-oxido-λ$^4$-sulfanylidenecyanamid (3)

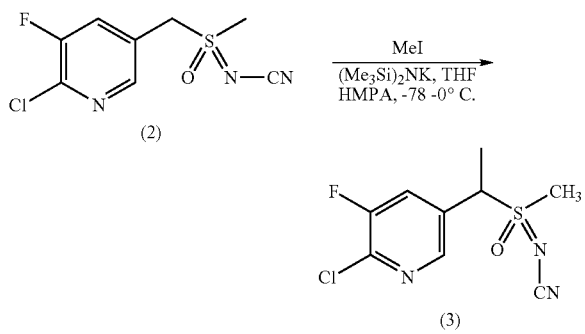

To a solution of N-cyanosulfoximine (2) (0.56 g, 2.0 mmol) and hexamethylphosphoramide (HMPA; 0.088 mL, 0.5 mmol) in anhydrous THF (20 mL) was added dropwise 0.5 M potassium bis(trimethylsilyl)amide in toluene (4.2 mL, 2.1 mmol) at −78° C. After 45 min, iodomethane (0.13 mL, 2.1 mmol) was added in one portion via a syringe. After 10 min, the temperature was allowed to rise to 0° C. and stirred for 1.5 h. The reaction was quenched with saturated aqueous NH$_4$Cl and diluted with brine. The mixture was extracted with EtOAc once followed by dichloromethane once. The combined organic layer was dried over Na$_2$SO$_4$, filtered and concentrated. The resulting mixture was purified on silica gel using 40% acetone in hexane to give. 0.49 g of [1-(5-fluoro-6-chloropyridin-3-yl)ethyl](methyl)-oxido-λ$^4$-sulfanylidenecyanamide (3) as colorless oil in 83% yield. $^1$H NMR (300 MHz, CDCl$_3$) δ 8.47 (m, 1H), 8.02 (m, 1H), 5.20 (m, 1H), 3.41 & 3.82 (2 s, 3H), 1.98-2.08 (m, 3H). LC-MS calcd. for $C_9H_9ClFN_3OS$ [M−1]$^+$: 260.70. Found: 260.10.

Example IV

Preparation of [1-(5-fluoro-6-methylthioyridin-3-yl)ethyl]-(methyl)-oxido-λ$^4$-sulfanylidenecyanamide (4)

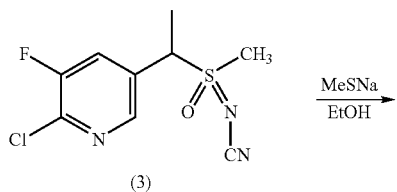

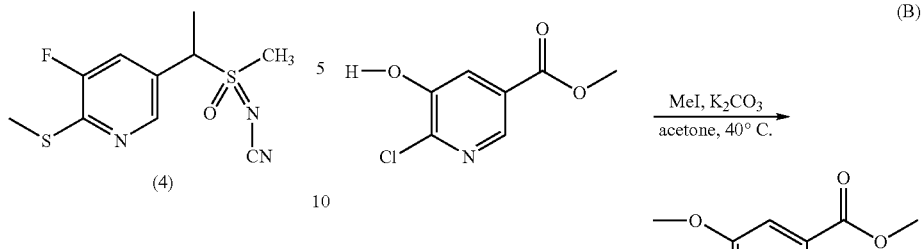

(4)

Using thiomethoxide displacement conditions similar to that described in Example I (C), 1-(5-fluoro-6-chloropyridin-3-yl)ethyl](methyl)-oxido-$\lambda^4$-sulfanylidenecyanamide (3) was reacted with sodium thiomethoxide (0.116 g, 1.66 mmol) in ethanol (10 mL) to give 0.093 g (25% yield) of the product [1-(5-fluoro-6-methylthioyridin-3-yl)ethyl](methyl)-oxido-$\lambda^4$-sulfanylidenecyanamide (4) as a mixture of disateremers. $^1$H NMR (300 MHz, CDCl$_3$) δ 8.34 (s, 1H), 7.37-7.44 (m, 1H), 4.66 (m, 1H), 3.07-3.13 (2 d, 3H), 1.90-1.98 (m, 3H). LC-MS calcd. for C$_{10}$H$_{12}$FN$_3$OS$_2$ [M−1]$^+$: 272.34. Found: 271.99.

Example V

Preparation of [(5-methoxy-6-chloropyridin-3-yl)methyl](methyl)-oxido-$\lambda^4$-sulfanylidenecyanamide (5)

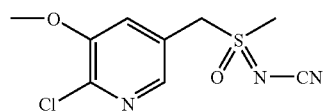

(5)

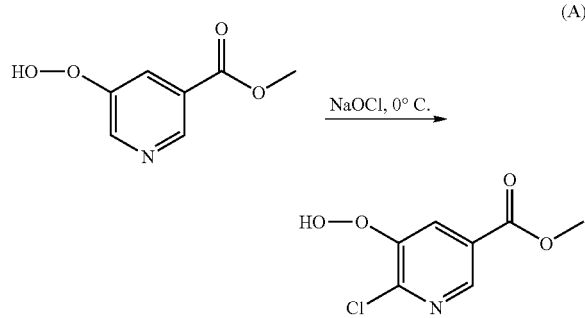

(A)

To a flask containing methyl-5-hydroxynicotinate (4.5 g, 29 mmol) was added sodium hypochlorite aqueous solution (6.15%, 26.7 mL, 22 mmol) dropwise under ice bath cooling. After 30 min of stirring, 2 M HCl (20 mL) was added and the resulting white crystals collected by filtration to give 2.31 g of 6-chloro-5-hydroxynicotinic acid methyl ester in 42% yield. $^1$H NMR (400 MHz, CDCl$_3$) δ 10.32 (bs, 1H), 8.48 (d, 1H), 7.84 (d, 1H), 7.40 (s, 1H), 3.93 (s. 3H); LC-MS (ELSD): mass calcd for C$_7$H$_6$ClNO$_3$ [M]$^+$ 187. Found 187.

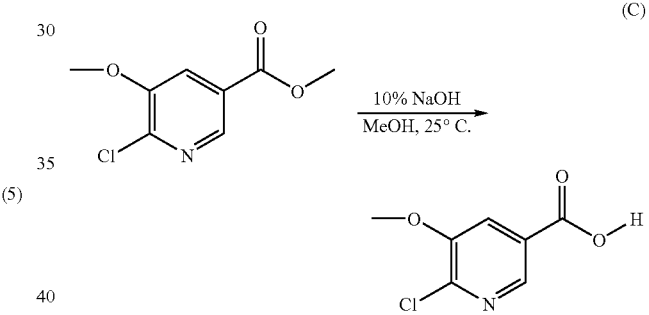

(B)

A mixture of 6-chloro-5-hydroxynicotinic acid methyl ester (1.8 g, 9.6 mmol), methyl iodide (2 M solution in Et$_2$O, 5.8 mL, 11.6 mmol) and potassium carbonate (2.0 g, 14.5 mmol) in acetone (190 mL) was refluxed for 6 h. The reaction was then concentrated via rotavap and H$_2$O was added (100 mL). The resulting white precipitate was filtered and rinsed with additional H$_2$O to furnish the product 6-chloro-5-methoxynicotinic acid methyl ester as a white solid (1.33 g, 68%); mp=83-85° C.; $^1$H NMR (400 MHz, CDCl$_3$) δ 8.60 (d, 1H), 7.77 (d, 1H), 3.98 (s, 3H), 3.96 (s, 3H): GC-MS: Exact mass calcd for C$_8$H$_8$ClNO$_3$ [M]$^+$, 201. Found 201.

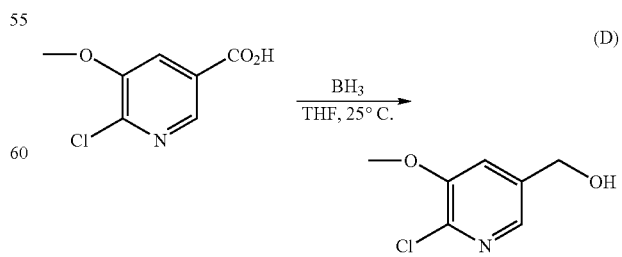

(C)

To a solution of 6-chloro-5-methoxynicotinic acid methyl ester (1.3 g, 6.4 mmol) in MeOH (4 mL) at 25° C. was added 10% NaOH aqueous solution (19.3 mmol). The reaction was stirred for 24 h, then placed into an ice water bath and acidified with 2M HCl until pH=2 was achieved. The flask was then placed into a refrigerator for 3 h. The white precipitate was filtered off and rinsed with cold H$_2$O. The solid was dissolved in acetone, dried over MgSO$_4$ and concentrated to furnish the product 6-chloro-5-methoxynicotinic acid as a yellow solid (0.895 g, 74%); $^1$H NMR (400 MHz, CDCl$_3$) δ 8.45 (d, 1H), 7.66 (d, 1H), 3.83 (s, 3H).

(D)

To a suspension of 6-chloro-5-methoxynicotinic acid (0.54 g, 2.9 mmol) in THF (5 mL) at 25° C. was added borane (1.0

M in THF, 5.8 mL, 5.8 mmol) dropwise. The mixture was let stir for 5 h, after which TLC showed complete conversion. The reaction was quenched with 2 M HCl until bubbling subsided and mixture extracted with dichloromethane (3×). The combined organic layers were dried over MgSO$_4$ and concentrated to furnish the product (6-chloro-5-methoxypyridin-3-yl)methanol as a white solid (0.49 mg (97%); mp 60-63° C.; $^1$H NMR (400 MHz, CDCl$_3$) δ 7.95 (d, 1H), 7.30 (d, 1H), 4.74 (s, 2H), 3.94 (s, 3H): LC-MS (ELSD): Exact mass calcd for C$_7$H$_8$ClNO$_2$ [M]$^+$, 173. Found 173.

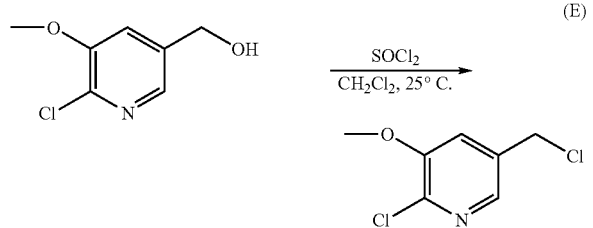

(E)

To a solution of (6-chloro-5-methoxypyridin-3-yl)methanol (0.50 g, 2.9 mmol) in dichloromethane (14 mL) at 25° C. was added thionyl chloride (230 μL, 3.2 mmol) dropwise. Let stir for 5 h, then the reaction was quenched with saturated aqueous NaHCO$_3$ and extracted with dichloromethane (3×). The combined organic layer were dried over MgSO$_4$ and concentrated to furnish the product 2-chloro-5-chloromethyl-3-methoxypyridine that was 96% pure by GC-MS. The product was used immediately in the next step without further purification. GC-MS: Exact mass calcd for C$_7$H$_7$Cl$_2$NO [M]$^+$, 191. Found 191.

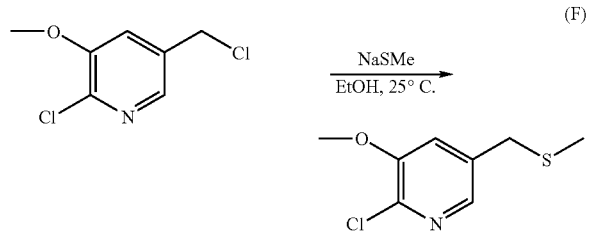

(F)

To a suspension of sodium thiomethoxide (0.24 g, 3.5 mmol) in ethanol (10 mL) at 25° C. was added solution of 2-chloro-5-chloromethyl-3-methoxypyridine (0.55 mg, 2.9 mmol) in EtOH (4 mL). The solution was stirred overnight, after which the reaction was concentrated under vacuum. The crude reaction mixture was partitioned between H$_2$O and Et$_2$O and the layers separated. The aqueous phase was further extracted with Et$_2$O (3×) and the combined organic phases dried over MgSO$_4$ and concentrated to furnish 2-chloro-3-methoxy-5-methylthiomethylpyridine as a yellow oil (0.42 g, 71% over two steps). GC-MS: Exact mass calcd for C$_8$H$_{10}$ClNOS [M]$^+$, 203. Found 203.

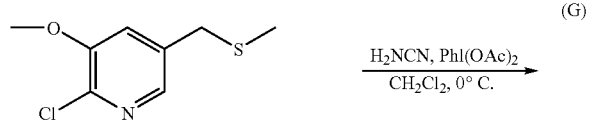

(G)

To a solution of 2-chloro-3-methoxy-5-methylthiomethylpyridine (0.42 g, 2.1 mmol) and cyanamide (172 mg, 4.1 mmol) in dichloromethane (8 mL) at 0° C. was added iodobenzenediacetate (726 mg, 2.3 mmol) all at once. The reaction was stirred for 2 h, then the reaction was concentrated and purified by flash chromatography to furnish the sulfilimine [1-(5-methoxy-6-chloropyridin-3-yl)methyl](methyl)-λ$^4$-sulfanylidenecyanamide as a light orange solid (0.25 g, 51%); mp 103-105° C.; $^1$H NMR (400 MHz, CDCl$_3$) δ7.96 (d, 1H), 7.34 (d, 1H), 4.34 (d, 1H), 4.16 (d, 1H), 3.99 (s, 3H), 2.85 (s, 3H): LC-MS (ELSD): Exact mass calcd for C$_9$H$_{11}$ClN$_3$OS [M+H]$^+$, 244. Found 244.

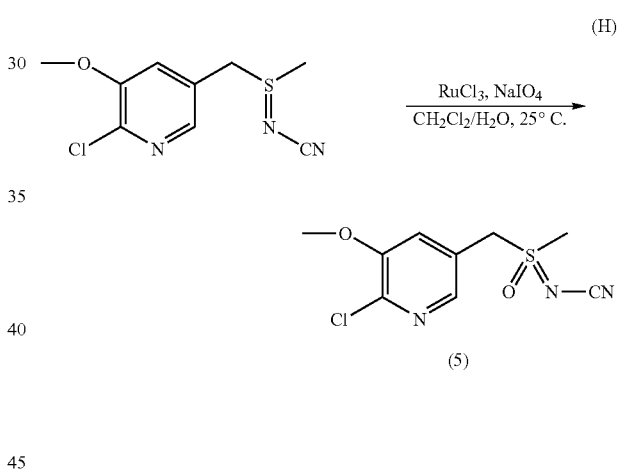

To a solution of NaIO$_4$ (0.35 g, 1.6 mmol) in H$_2$O (3 mL) at 25° C. was added dichloromethane (3 mL) followed by RuCl$_3$.H$_2$O (5 mg, 0.021 mmol). To the dark brown mixture was then added solution of sulfilimine [1-(5-methoxy-6-chloropyridin-3-yl)methyl](methyl)-λ$^4$-sulfanylidenecyanamide (0.2 g, 0.82 mmol) in dichloromethane (2 mL) dropwise over course of 15 mm. The mixture was stirred for 30 mm, after which TLC showed complete conversion. The crude reaction mixture was filtered through filter paper (No. 1) which removed most of the discoloration and the resulting biphasic mixture was separated. The aqueous phase was further extracted with dichloromethane and the combined organic extracts were washed with H$_2$O and brine, dried over Na$_2$SO$_4$, and concentrated to furnish the sulfoximine [(5-methoxy-6-chloropyridin-3-yl)methyl](methyl)-oxido-λ$^4$-sulfanylidenecyanamide (5) as a white solid (0.13 g, 62%); mp 123-125° C.; $^1$H NMR (400 MHz, CDCl$_3$) δ 7.98 (d, 1H), 7.41 (d, 1H), 4.63 (m, 2H), 3.99 (s, 3H), 3.11 (s, 3H): LC-MS (ELSD): Exact mass calcd for C$_9$H$_{11}$ClN$_3$O$_2$S [M+H]$^+$, 260. Found 260.

Example VI

Preparation of [1-(5-methoxy-6-chloropyridin-3-yl)ethyl](methyl)-oxido-λ⁴-sulfanylidenecyanamide (6)

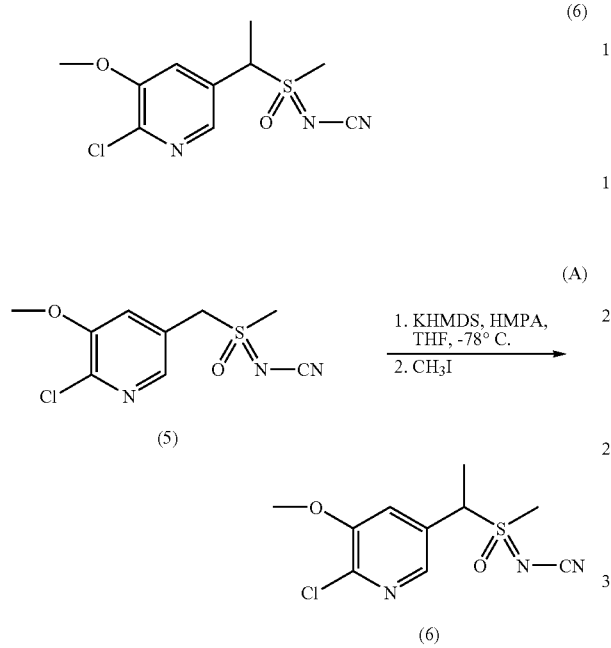

To a solution of sulfoximine (5) (0.07 g, 0.27 mmol) and hexamethyl-phosphoramide (HMPA; 23 μL, 0.14 mmol) in THF (3 mL) at −78° C. was added potassium hexamethyldisilazane (KHMDS; 0.5 M in toluene, 590 μL, 0.30 mmol) dropwise. The solution was stirred at −78° C. for an additional 20 min, after which iodomethane (15 μL, 0.30 mmol) was added. The reaction was allowed to warm to room temperature over the course of 4 hr, after which it was quenched with saturated aqueous NH$_4$Cl and extracted with dichloromethane. The organic layer was dried over MgSO$_4$ and concentrated to furnish the sulfoximine (6) as a yellow oil (0.33 g, 45%) and a 1:1 mixture of diastereomers; $^1$H NMR (400 MHz, CDCl$_3$) δ 7.99 (m, 2H), 7.41 (d, 1H), 7.37 (d, 1H), 4.61 (m, 2H), 4.00 (s, 3H), 3.99 (s, 3H), 3.05 (s, 3H), 3.01 (s, 3H), 2.00 (d, 3H), 1.98 (d, 3H); LC-MS (ELSD): Exact mass calcd for C$_{10}$H$_{13}$ClN$_3$O$_2$S [M+H]$^+$, 274. Found 274.

Example VII

Preparation of [(5-bromo-6-chloropyridin-3-yl)methyl](methyl)-oxido-λ⁴-sulfanylidenecyanamide (7)

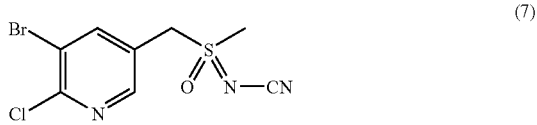

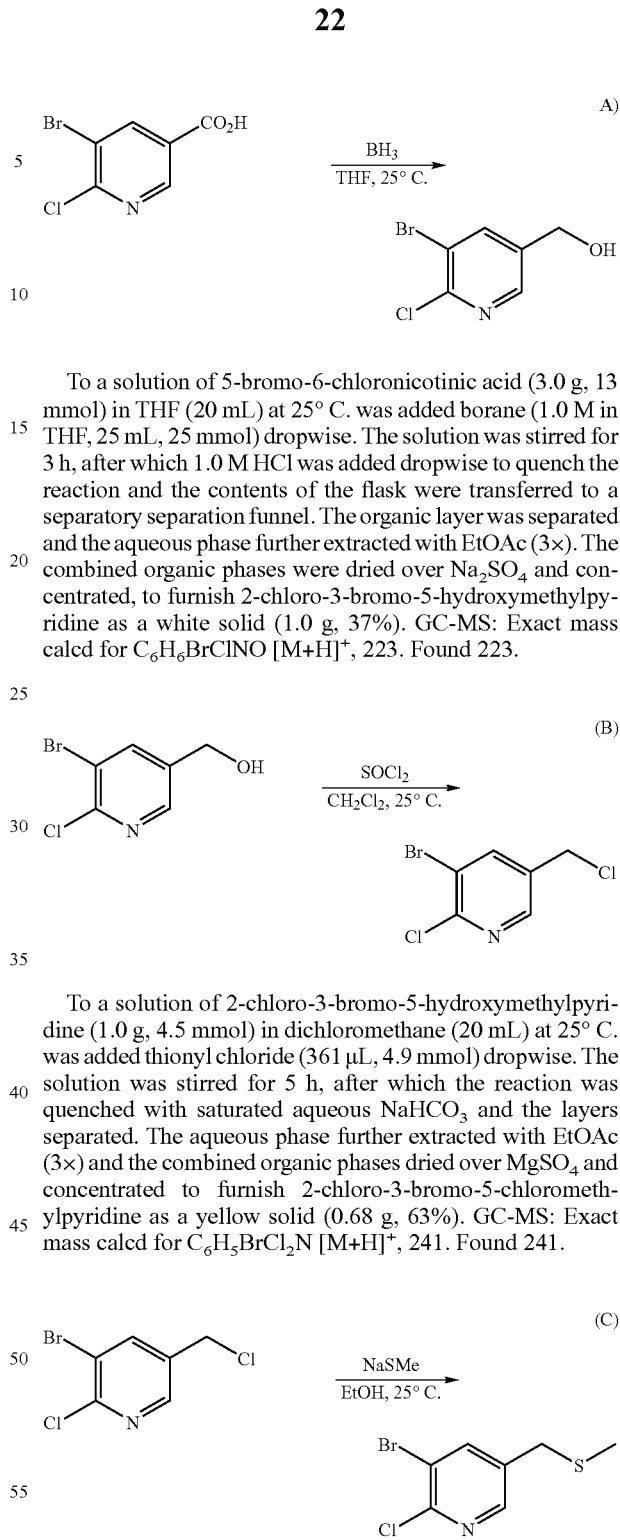

To a solution of 5-bromo-6-chloronicotinic acid (3.0 g, 13 mmol) in THF (20 mL) at 25° C. was added borane (1.0 M in THF, 25 mL, 25 mmol) dropwise. The solution was stirred for 3 h, after which 1.0 M HCl was added dropwise to quench the reaction and the contents of the flask were transferred to a separatory separation funnel. The organic layer was separated and the aqueous phase further extracted with EtOAc (3×). The combined organic phases were dried over Na$_2$SO$_4$ and concentrated, to furnish 2-chloro-3-bromo-5-hydroxymethylpyridine as a white solid (1.0 g, 37%). GC-MS: Exact mass calcd for C$_6$H$_6$BrClNO [M+H]$^+$, 223. Found 223.

To a solution of 2-chloro-3-bromo-5-hydroxymethylpyridine (1.0 g, 4.5 mmol) in dichloromethane (20 mL) at 25° C. was added thionyl chloride (361 μL, 4.9 mmol) dropwise. The solution was stirred for 5 h, after which the reaction was quenched with saturated aqueous NaHCO$_3$ and the layers separated. The aqueous phase further extracted with EtOAc (3×) and the combined organic phases dried over MgSO$_4$ and concentrated to furnish 2-chloro-3-bromo-5-chloromethylpyridine as a yellow solid (0.68 g, 63%). GC-MS: Exact mass calcd for C$_6$H$_5$BrCl$_2$N [M+H]$^+$, 241. Found 241.

To a suspension of sodium thiomethoxide (0.2 g, 2.8 mmol) in ethanol (6 mL) at 25° C. was added solution of 2-chloro-3-bromo-5-chloromethylpyridine (0.68 g, 2.8 mmol) in EtOH (4 mL). The solution was stirred for 4 h, after which the reaction was concentrated under vacuum. The crude reaction mixture was partitioned between H$_2$O and Et$_2$O and the layers separated. The aqueous phase was further extracted with Et$_2$O (3×) and the combined organic phases dried over MgSO$_4$, concentrated and purified via flash chromatography to furnish sulfide 2-chloro-3-bromo-5-methylthiomethylpyridine as a colorless oil (0.22 g, 31%).

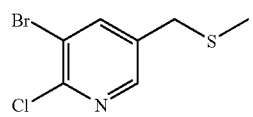

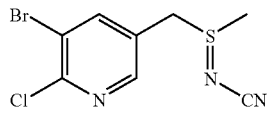

To a solution of 2-chloro-3-bromo-5-methylthiomethylpyridine (0.22 g, 0.9 mmol) and cyanamide (0.074 g, 1.8 mmol) in dichloromethane (4 mL) at 0° C. was added iodobenzenediacetate (0.31 g, 1.0 mmol) all at once. The reaction was stirred for 2 h, then the reaction was concentrated and triturated with dichloromethane to furnish the sulfilimine [1-(5-bromo-6-chloropyridin-3-yl)methyl](methyl)-$\lambda^4$-sulfanylidenecyanamide as an orange solid (0.17 g, 66%).

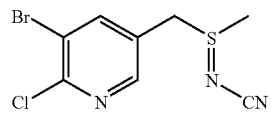

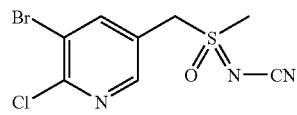

To a solution of NaIO$_4$ (0.25 g, 1.2 mmol) in H$_2$O (3 mL) at 25° C. was added dichloromethane (3 mL) followed by RuCl$_3$.H$_2$O (0.0066 g, 0.029 mmol). To the dark brown mixture was then added solution of [1-(5-bromo-6-chloropyridin-3-yl)methyl](methyl)-$\lambda^4$-sulfanylidenecyanamide (0.17 g, 0.6 mmol) in CH$_2$Cl$_2$ (2 mL) dropwise over course of 15 mm. The mixture was stirred for 1 h, after which TLC showed complete conversion. The reaction was diluted with dichloromethane (5 mL) and passed through celite plug. The filtrate was separated and the H$_2$O layer further extracted with dichloromethane. The combined organic layers were dried over MgSO$_4$ and concentrated to furnish the sulfoximine (7) as a white solid (0.083 g, 46%); mp=139-142° C. $^1$H NMR (400 MHz, CDCl$_3$/DMSO) δ 8.6 (d, 1H), 8.4 (d, 1H), 5.1 (s, 2H), 3.5 (s, 3H); LC-MS (ELSD): Exact mass calcd for C$_8$H$_7$BrClN$_3$OS [M]$^+$, 308. Found 308.

Example VIII

Preparation of [1-(5-bromo-6-chloropyridin-3-yl)ethyl](methyl)-oxido-$\lambda^4$-sulfanylidenecyanamide (8)

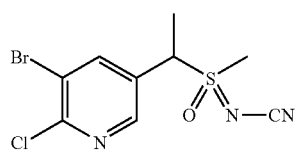

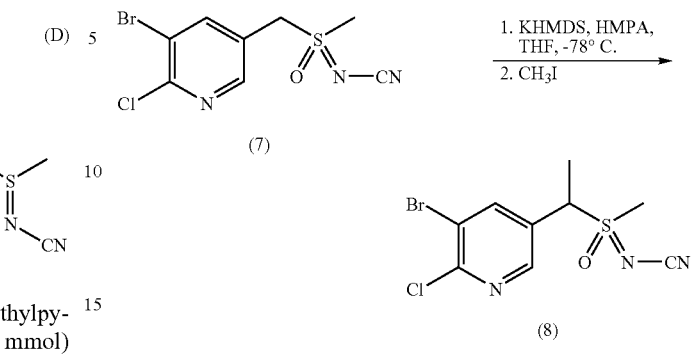

To a solution of sulfoximine (7) (0.050 g, 0.16 mmol) in THF (2 mL) at −78° C. was added KHMDS (0.5 M in toluene, 360 μL, 0.18 mmol) dropwise. The solution was stirred at −78° C. for an additional 20 min, after which iodomethane (11 μL, 0.18 mmol) was added. The reaction was allowed to warm to room temperature over the course of 2 hr, after which it was quenched with saturated aqueous NH$_4$Cl and extracted with dichloromethane. The organic layer was dried over MgSO$_4$, concentrated, and the crude product triturated with Et$_2$O to furnish the sulfoximine (8) as a white solid (0.023 g, 43%); $^1$H NMR (400 MHz, CDCl$_3$/DMSO) δ 8.6 (d, 1H), 8.4 (d, 1H), 5.1 (s, 2H), 3.5 (s, 3H); LC-MS (ELSD): mass calcd for C$_9$H$_{10}$BrClN$_3$OS [M+H]$^+$ 323. Found 323.

Example IX

Preparation of [(4,6-dichloropyridin-3-yl)methyl](methyl)-oxido $\lambda^4$-sulfanylidenecyanamide (9)

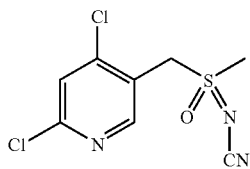

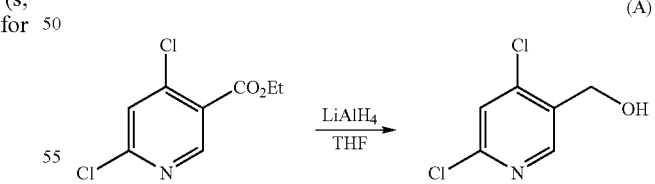

To a stirred solution of ethyl 4,6-dichloronicotinate (8.8 g, 40 mmol) in anhydrous THF (75 mL) cooled in an ice-water bath was added in a dropwise fashion 1 M LiAlH$_4$ solution in THF (25 mL, 25 mmol). During the addition, the temperature was not allowed to rise above 25° C. After the addition was over, the reaction was warmed to 40° C. for 15 min, cooled, then quenched by the successive dropwise addition of water (0.95 mL), 15% aqueous NaOH (0.95 mL) and water (1.85 mL). The mixture was filtered through celite and the filtrated was dried (MgSO$_4$), passed through a short pad of silica gel and concentrated to give a red oil. Ether (100 mL) was added whereupon a gummy precipitate immediately appeared, which was removed by filtration. The ether solution was allowed to stand at room temperature overnight, during which time more precipitate was formed which was removed again by filtration. The ether solution was concentrated and dried to give 3.25 g of the product 2,4-dichloro-5-hydroxy-methylpyridine in 46% yield as a nearly colorless oily solid. $^1$H NMR (300 MHz, CDCl$_3$) δ 8.5 (s, 1H), 7.4 (s, 1H), 4.8 (s, 2H), 2.7 (bs, 1H); GC-MS: mass calcd for C$_6$H$_5$Cl$_2$NO [M]$^+$, 177. Found 177.

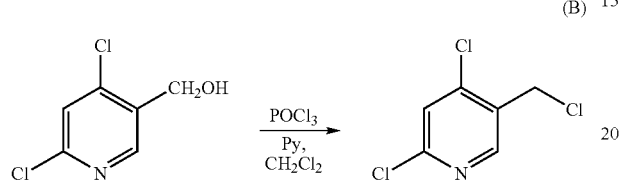
(B)

The starting material 2,4-dichloro-5-hydroxymethylpyridine (3.2 g, 18 mmol) was converted into 2.0 g of 2,4-dichloro-5-chloromethylpyridine (57% yield) as a yellow oil using the same procedure as describe in Example I, Procedure B. $^1$H NMR (300 MHz, CDCl$_3$) δ 8.4 (s, 1H), 7.4 (s, 1H), 4.7 (s, 2H); GC-MS: mass calcd for C$_6$H$_4$Cl$_3$N [M]$^+$, 195. Found 195.

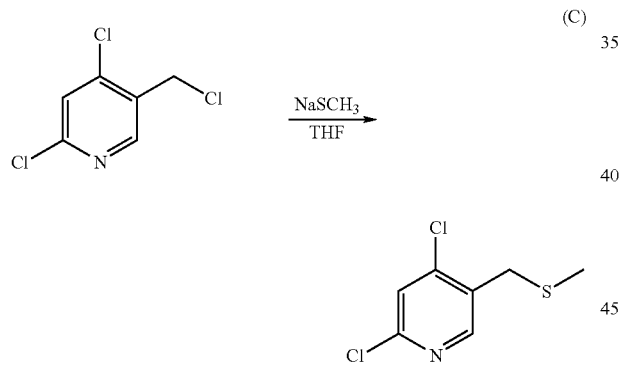
(C)

2,4-Dichloro-5-methylthiomethylpyridine (2.0 g, 94% yield) was prepared as a yellow oil from 2,4-dichloro-5-chloromethylpyridine (2.0 g, 1.0 mmol) by using the same method as described in Example I, procedure C. $^1$H NMR (300 MHz, CDCl$_3$) δ 8.3 (s, 1H), 7.4 (s, 1H), 3.7 (s, 2H), 2.0 (s, 3H); GC-MS: mass calcd for C$_7$H$_7$Cl$_2$NS [M]$^+$, 207. Found 207.

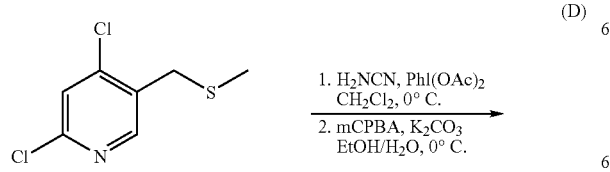
(D)

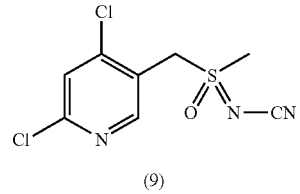
(9)

[(4,6-Dichloropyridin-3-yl)methyl](methyl)-oxido λ$^4$-sulfanylidene-cyanamide (9, 0.78 g, 52% yield) was prepared as a white solid from 2,4-dichloro-5-methylthiomethylpyridine in a two step sequence using the same method as described in Example I, procedures D and E. $^1$H NMR (300 MHz, CDCl$_3$) δ 8.6 (s, 1H), 7.6 (s, 1H), 4.9 (m, 2H), 3.3 (s, 3H); LC-MS (ELSD): mass calcd for C$_8$H$_7$Cl$_2$N$_3$OS [M]$^+$, 263. Found 263.

Example X

Insecticidal Testing

The compounds identified in the foregoing examples were tested against cotton aphid and green peach aphid using procedures described hereinafter.

Insecticidal Test for Cotton Aphid (*Aphis gossypii*) in Foliar Spray Assay

Squash with fully expanded cotyledon leaves were trimmed to one cotyledon per plant and infested with cotton aphid (wingless adult and nymph) 1 day prior to chemical application. Each plant was examined before chemical application to ensure proper infestation (ca. 30-70 aphids per plant). Compounds (2 mg) were dissolved in 2 ml of acetone: methanol (1:1) solvent, forming stock solutions of 1000 ppm. The stock solutions were diluted 5× with 0.025% Tween 20 in H$_2$O to obtain the highest test solution at 200 ppm. Lower test concentrations (50, 12.5, 3.13 and 0.78 ppm) were prepared by making sequential 4× dilutions from the 200 ppm solution with a diluent consisting 80 parts of 0.025% Tween 20 in H$_2$O and 20 parts of acetone:methanol (1:1). A hand-held Devilbiss sprayer was used to apply the spray solutions until runoff to both sides of the squash cotyledon leaves. Four plants (4 replications) were used for each concentration of each compound. Reference plants (solvent check) were sprayed with the diluent only. Treated plants were held in a holding room for 3 days at approximately 23° C. and 40% RH before the number of live aphids on each plant was recorded. Insecticidal activity was measured by Corrected % Control using Abbott's correction formula:

Corrected % Control=100*(X−Y)/X where
X=No. of live aphids on solvent check plants
Y=No. of live aphids on treated plants Insecticidal Test for Green Peach Aphid (*Myzus persicae*) in Foliar Spray Assay Cabbage seedlings grown in 3-inch pots, with 2-3 small (3-5 cm) true leaves, were used as test substrate. The seedlings were infested with 20-50 green peach aphids (wingless adult and nymph) 2-3 days prior to chemical application. Four seedlings were used for each treatment. Compounds (2 mg) were dissolved in 2 ml of acetone:methanol (1:1) solvent, forming stock solutions of 1000 ppm. The stock solutions were diluted 5× with 0.025% Tween 20 in H$_2$O to obtain the highest test solution at 200 ppm. A lower test concentration of 50 ppm was prepared by making a 4× dilution from the 200 ppm solution with a diluent consisting 80 parts of 0.025% Tween 20 in H₂O and 20 parts of acetone: methanol (1:1). A hand-held Devilbiss sprayer was used for spraying a solution to both sides of cabbage leaves until runoff. Reference plants (solvent check) were sprayed with the diluent only. Treated plants were held in a holding room for three days at approximately 23° C. and 40% RH prior to grading. Evaluation was conducted by counting the number of live aphids per plant under a microscope. Insecticidal activity was measured by using Abbott's correction formula:

Corrected % Control=100*(X−Y)/X where

X=No. of live aphids on solvent check plants

Y=No. of live aphids on treated plants

The Corrected % Control values from the above assays are given in Table 1.

TABLE 1

| Comp # | CA 200 | CA 50 | GPA 200 | GPA 50 |
|---|---|---|---|---|
| 1 | A | A | H | G |
| 2 | A | A | B | E |
| 3 | A | A | A | B |
| 4 | A | B | G | G |
| 5 | A | C | G | G |
| 6 | A | D | G | G |
| 7 | A | A | G | G |
| 8 | A | A | B | G |
| 9 | A | A | H | G |

CA 200 refers to % control at 200 ppm against cotton aphid in foliar spray tests,
CA 50 refers to % control at 50 ppm against cotton aphid in foliar spray tests,
GPA 200 refers to % control at 200 ppm against green peach aphid in foliar spray tests,
GPA 50 refers to % control at 50 ppm against green peach aphid in foliar spray tests.

In each case of Table 1 the rating scale is as follows:

| % Control (or Mortality) | Rating |
|---|---|
| 90-100 | A |
| 80-89 | B |
| 70-79 | C |
| 60-69 | D |
| 50-59 | E |
| Less than 50 | F |
| Inactive | G |
| Not tested | H |

The compounds that showed activity against both aphid species in Table 1 were further tested with multiple lower doses (rundown assays) against cotton aphid using procedures described hereinafter. Results are shown in Table 2.

TABLE 2

| | % Control at ppm against cotton aphid (foliar spray) | | | |
|---|---|---|---|---|
| Comp # | CA 0.78 | CA 3.13 | CA 12.5 | CA 50 |
| 2 | A | A | A | A |
| 3 | A | A | A | A |
| 8 | E | A | A | A |

In each case of Table 2 the rating scale is the same as that used for Table 1.

Insecticide Utility

The compounds of the invention are useful for the control of invertebrates including insects. Therefore, the present invention also is directed to a method for inhibiting an insect which comprises applying an insect-inhibiting amount of a compound of formula (I) to a locus of the insect, to the area to be protected, or directly on the insect to be controlled. The compounds of the invention may also be used to control other invertebrate pests such as mites and nematodes.

The "locus" of insects or other pests is a term used herein to refer to the environment in which the insects or other pests live or where their eggs are present, including the air surrounding them, the food they eat, or objects which they contact. For example, insects which eat, damage or contact edible, commodity, ornamental, turf or pasture plants can be controlled by applying the active compounds to the seed of the plant before planting, to the seedling, or cutting which is planted, the leaves, stems, fruits, grain, and/or roots, or to the soil or other growth medium before or after the crop is planted. Protection of these plants against virus, fungus or bacterium diseases may also be achieved indirectly through controlling sap-feeding pests such as whitefly, plant hopper, aphid and spider mite. Such plants include those which are bred through conventional approaches and which are genetically modified using modern biotechnology to gain insect-resistant, herbicide-resistant, nutrition-enhancement, and/or any other beneficial traits.

It is contemplated that the compounds might also be useful to protect textiles, paper, stored grain, seeds and other foodstuffs, houses and other buildings which may be occupied by humans and/or companion, farm, ranch, zoo, or other animals, by applying an active compound to or near such objects. Domesticated animals, buildings or human beings might be protected with the compounds by controlling invertebrate and/or nematode pests that are parasitic or are capable of transmitting infectious diseases. Such pests include, for example, chiggers, ticks, lice, mosquitoes, flies, fleas and heartworms. Nonagronomic applications also include invertebrate pest control in forests, in yards, along road sides and railroad right of way.

The term "inhibiting an insect" refers to a decrease in the numbers of living insects, or a decrease in the number of viable insect eggs. The extent of reduction accomplished by a compound depends, of course, upon the application rate of the compound, the particular compound used, and the target insect species. At least an inactivating amount should be used. The term "insect-inactivating amount" is used to describe the amount, which is sufficient to cause a measurable reduction in the treated insect population. Generally an amount in the range from about 1 to about 1000 ppm by weight active compound is used. For example, insects or other pests which can be inhibited include, but are not limited to:

Lepidoptera—*Heliothis* spp., *Helicoverpa* spp., *Spodoptera* spp., *Mythimna unipuncta, Agrotis ipsilon, Earias* spp., *Euxoa auxiliaris, Trichoplusia ni, Anticarsia gemmatalis, Rachiplusia nu, Plutella xylostella, Chilo* spp., *Scirpophaga incertulas, Sesamia inferens, Cnaphalocrocis medinalis, Ostrinia nubilalis, Cydia pomonella, Carposina niponensis, Adoxophyes orana, Archips argyrospilus, Pandemis heparana, Epinotia aporema, Eupoecilia ambiguella, Lobesia botrana, Polychrosis viteana, Pectinophora gossypiella, Pieris rapae, Phyllonorycter* spp., *Leucoptera malifoliella, Phyllocnisitis citrella*

Coleoptera—*Diabrotica* spp., *Leptinotarsa decemlineata, Oulema oryzae, Anthonomus grandis, Lissorhoptrus oryzophilus, Agriotes* spp., *Melanotus communis, Popillia japonica, Cyclocephala* spp., *Tribolium* spp.

Homoptera—*Aphis* spp., *Myzus persicae, Rhopalosiphum* spp., *Dysaphis plantaginea, Toxoptera* spp., *Macrosiphum euphorbiae, Aulacorthum solani, Sitobion avenae, Metopolophium dirhodum, Schizaphis graminum, Brachycolus noxius, Nephotettix* spp., *Nilaparvata lugens, Sogatella furcifera, Laodelphax striatellus, Bemisia tabaci, Trialeurodes vaporariorum, Aleurodes proletella, Aleurothrixus floccosus, Quadraspidiotus perniciosus, Unaspis yanonensis, Ceroplastes rubens, Aonidiella aurantii*

Hemiptera—*Lygus* spp., *Eurygaster maura, Nezara viridula, Piezodorus guildingi, Leptocorisa varicornis, Cimex lectularius, Cimex hemipterus*

Thysanoptera—*Frankliniella* spp., *Thrips* spp., *Scirtothrips dorsalis*

Isoptera—*Reticulitermes flavipes, Coptotermes formosanus, Reticulitermes virginicus, Heterotennes aureus, Reticulitermes hesperus, Coptotermes frenchii, Shedorhinotermes* spp., *Reticulitermes santonensis, Reticulitermes grassei, Reticulitermes banyulensis, Reticulitermes speratus, Reticulitermes hageni, Reticulitermes tibialis, Zootermopsis* spp., *Incisitermes* spp., *Marginitermes* spp., *Macrotermes* spp., *Microcerotermes* spp., *Microtermes* spp.

Diptera—*Liriomyza* spp., *Musca domestica, Aedes* spp., *Culex* spp., *Anopheles* spp., *Fannia* spp., *Stomoxys* spp., Hymenoptera—*Iridomyrmex humilis, Solenopsis* spp., *Monomorium pharaonis, Atta* spp., *Pogonomyrmex* spp., *Camponotus* spp., *Monomorium* spp., *Tapinoma sessile, Tetramorium* spp., *Xylocapa* spp., *Vespula* spp., *Polistes* spp.

Mallophaga (chewing lice)

Anoplura (sucking lice)—*Pthirus pubis, Pediculus* spp.

Orthoptera (grasshoppers, crickets)—*Melanoplus* spp., *Locusta migratoria, Schistocerca gregaria*, Gryllotalpidae (mole crickets).

Blattoidea (cockroaches)—*Blatta orientalis, Blattella germanica, Periplaneta americana, Supella longipalpa, Periplaneta australasiae, Periplaneta brunnea, Parcoblatta pennsylvanica, Periplaneta fuliginosa, Pycnoscelus surinamensis,*

Siphonaptera—*Ctenophalides* spp., *Pulex irritans*

Acari—*Tetranychus* spp., *Panonychus* spp., *Eotetranychus carpini, Phyllocoptruta oleivora, Aculus pelekassi, Brevipalpus phoenicis, Boophilus* spp., *Dermacentor variabilis, Rhipicephalus sanguineus, Amblyomma americanum, Ixodes* spp., *Notoedres cati, Sarcoptes scabiei, Dermatophagoides* spp.

Nematoda—*Dirofilaria immitis, Meloidogyne* spp., *Heterodera* spp., *Hoplolaimus columbus, Belonolaimus* spp., *Pratylenchus* spp., *Rotylenchus reniformis, Criconemella ornata, Ditylenchus* spp., *Aphelenchoides besseyi, Hirschmanniella* spp.

Compositions

The compounds of this invention are applied in the form of compositions which are important embodiments of the invention, and which comprise a compound of this invention and a phytologically-acceptable inert carrier. Control of the pests is achieved by applying compounds of the invention in forms of sprays, topical treatment, gels, seed coatings, microcapsulations, systemic uptake, baits, eartags, boluses, foggers, fumigants aerosols, dusts and many others. The compositions are either concentrated solid or liquid formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and/or nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Systemic movement of compounds of the invention in plants may be utilized to control pests on one portion of the plant by applying the compounds to a different portion of it. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal proteins, those expressing herbicide resistance, such as "Roundup Ready®" seed, or those with "stacked" foreign genes expressing insecticidal proteins, herbicide resistance, nutrition-enhancement and/or any other beneficial traits.

An insecticidal bait composition consisting of compounds of the present invention and attractants and/or feeding stimulants may be used to increase efficacy of the insecticides against insect pest in a device such as trap, bait station, and the like. The bait composition is usually a solid, semi-solid (including gel) or liquid bait matrix including the stimulants and one or more non-microencapsulated or microencapsulated insecticides in an amount effective to act as kill agents.

The compounds of the present invention (Formula I) are often applied in conjunction with one or more other insecticides or fungicides or herbicides to obtain control of a wider variety of pests diseases and weeds. When used in conjunction with other insecticides or fungicides or herbicides, the presently claimed compounds can be formulated with the other insecticides or fungicides or herbicide, tank mixed with the other insecticides or fungicides or herbicides, or applied sequentially with the other insecticides or fungicides or herbicides.

Some of the insecticides that can be employed beneficially in combination with the compounds of the present invention include: antibiotic insecticides such as allosamidin and thuringiensin; macrocyclic lactone insecticides such as spinosad, spinetoram, and other spinosyns including the 21-butenyl spinosyns and their derivatives; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; biological insecticides such as *Bacillus popilliae, B. sphaericus, B. thuringiensis* subsp. *aizawai, B. thuringiensis* subsp. *kurstaki, B. thuringiensis* subsp. *tenebrionis, Beauveria bassiana, Cydia pomonella* granulosis virus, Douglas fir tussock moth NPV, gypsy moth NPV, *Helicoverpa zea* NPV, Indian meal moth granulosis virus, *Metarhizium anisopliae, Nosema locustae, Paecilomyces fumosoroseus, P. lilacinus, Photorhabdus luminescens, Spodoptera exigua* NPV, trypsin modulating oostatic factor, *Xenorhabdus nematophilus*, and *X. bovienii*, plant incorporated protectant insecticides such as Cry1Ab, Cry1Ac, Cry1F, Cry1A. 105, Cry2Ab2, Cry3A, mir Cry3A, Cry3Bb1, Cry34, Cry35, and VIP3A; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methyl-chloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemetonmethyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphosethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophosethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spirodiclofen, spiromesifen and spirotetramat; thiourea insecticides such as diafenthiuron; urea insecticides such as flucofuron and sulcofuron; and unclassified insecticides such as AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene and triazamate and any combinations thereof.

Some of the fungicides that can be employed beneficially in combination with the compounds of the present invention include: 2-(thiocyanatomethylthio)benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium* minitans, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, *Reynoutria sachalinensis* extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanatemethyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmediphamethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, flurochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

We claim:

1. A compound of the formula (I)

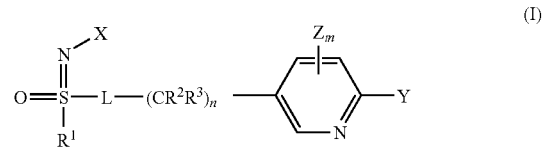

wherein

X represents CN or $NO_2$;

Y represents halogen, $C_1$-$C_4$ alkyl, $C_1$-$C_4$ haloalkyl, $C_1$-$C_4$ alkoxy, $C_1$-$C_4$ haloalkoxy, CN or $NO_2$;

Z represents halogen, $C_1$-$C_4$ alkyl, $C_1$-$C_4$ alkoxy, $C_1$-$C_4$ haloalkyl, or haloalkoxy;

m represents an integer from 1-3;

L represents a single bond;

$R^1$ represents $C_1$-$C_4$ alkyl;

$R^2$ and $R^3$ independently represent hydrogen, halogen, or $C_1$-$C_4$ alkyl;

n represents an integer from 0-3.

2. A compound of claim 1 wherein Z represents halogen and m represents 1.

3. A compound of claim 1 wherein X represents $NO_2$ or CN.

4. A compound of claim 1 wherein $R^2$ and $R^3$ independently represent hydrogen or $C_1$-$C_4$ alkyl.

5. A compound of claim 1 wherein $R^1$ represents $CH_3$, L represents a single bond, i.e., having the structure:

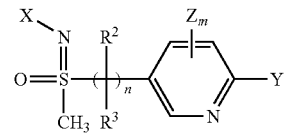

wherein n is an integer from 1-3, and X, Y, Z, $R^2$, $R^3$ and m are as previously defined.

6. A compound of claim 1 wherein Y represents halogen or $C_1$-$C_2$ alkyl.

7. A composition for controlling insects which comprises a compound of any one of claims 1-4, and 5-6 in combination with a phytologically-acceptable carrier.

* * * * *